United States Patent
Giger

Patent Number: 5,856,343
Date of Patent: Jan. 5, 1999

[54] IMIDAZOLYLMETHYL-PYRIDINES USED FOR SENILE DEMENTIA

[75] Inventor: Rudolf Karl Andreas Giger, Muttenz, Switzerland

[73] Assignee: Novartis AG, Basel, Switzerland

[21] Appl. No.: 819,460

[22] Filed: Mar. 17, 1997

Related U.S. Application Data

[62] Division of Ser. No. 421,098, Apr. 13, 1995, Pat. No. 5,635,521, which is a continuation of Ser. No. 216,213, Mar. 22, 1994, abandoned, which is a continuation-in-part of Ser. No. 125,097, Sep. 22, 1993, abandoned, which is a continuation of Ser. No. 948,368, Sep. 21, 1992, abandoned.

[30] Foreign Application Priority Data

Sep. 23, 1991 [DE] Germany ............... 41 31 584.7

[51] Int. Cl.$^6$ .................................... A61K 31/44
[52] U.S. Cl. .............................. 514/341; 546/272.7
[58] Field of Search ............................. 514/341

[56] References Cited

U.S. PATENT DOCUMENTS

| | | | |
|---|---|---|---|
| 3,417,091 | 12/1968 | Pickholz et al. | 514/341 |
| 3,993,643 | 11/1976 | Henry et al. | 548/315.7 |
| 4,230,714 | 10/1980 | Cross et al. | 514/341 |
| 4,404,387 | 9/1983 | Gall | 514/341 |
| 4,591,377 | 5/1986 | Leone-Bay et al. | 548/327 |
| 4,634,711 | 1/1987 | Kaiser et al. | 514/341 |
| 4,659,720 | 4/1987 | Chabala et al. | 514/313 |
| 4,925,851 | 5/1990 | Houlihan | 514/326 |
| 4,937,250 | 6/1990 | Bowman et al. | 514/341 |
| 5,021,434 | 6/1991 | Strehlke et al. | 514/341 |

FOREIGN PATENT DOCUMENTS

| | | |
|---|---|---|
| 3560 | 6/1979 | European Pat. Off. . |
| 29742 | 6/1981 | European Pat. Off. . |
| 113570 | 7/1984 | European Pat. Off. . |
| 131302 | 1/1985 | European Pat. Off. . |
| 159011 | 10/1985 | European Pat. Off. . |
| 244803 | 11/1987 | European Pat. Off. . |
| 270091 | 6/1988 | European Pat. Off. . |
| 293978 | 12/1988 | European Pat. Off. . |
| 91242 | 7/1972 | Germany . |
| 2651580 | 6/1978 | Germany . |
| 2222401 | 3/1990 | United Kingdom . |

OTHER PUBLICATIONS

Shutske Medicinal Chemistry Approaches To A.D and Other Dementias Symposium, Division of Educational Services, Mayo Clinic, 1993.
Annals, vol. 643, pp. 136–144 (1961).
J. Heterocyclic Chem., vol. 14, pp. 1279–1281 (1977).
Inorg. Chem., vol. 16, No. 6, pp. 1470–1476 (1977).
Derwent Abstract 86–140808.
Derwent Abstract 88–358545.
Derwent Abstract 90–096560.
Derwent Abstract 90–301291.

*Primary Examiner*—Jane Fan
*Attorney, Agent, or Firm*—Joseph J. Borovian

[57] ABSTRACT

Compounds of formula I,

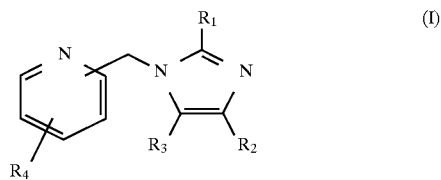

wherein $R_1$ to $R_4$ possess the significances given in the description, may be used in the treatment of senile dementia, Alzheimer's disease and depression.

5 Claims, No Drawings

IMIDAZOLYLMETHYL-PYRIDINES USED FOR SENILE DEMENTIA

This a division of application Ser. No. 08/421,098, filed Apr. 13, 1995, now issued as U.S. Pat. No. 5,635,521, which in turn is a continuation of application Ser. No. 08/216,213, filed Mar. 22, 1994, which in turn is a continuation-in-part of application Ser. No. 08/125,097, filed Sep. 22, 1993, which in turn is a continuation of application Ser. No. 07/948,368, filed Sep. 21, 1992, the latter three of which are now abandoned.

The present invention relates to imidazolylmethyl-pyridines, their production, their use as pharmaceuticals and pharmaceutical compositions containing them.

More particularly, the present invention provides compounds of formula I,

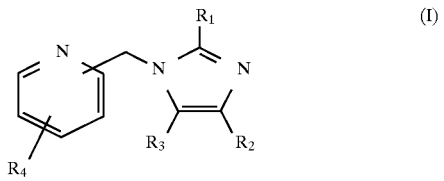

wherein
- $R_1$ is alkyl (1–4 C), halogen with an atomic number of 9 to 35 or amino optionally mono- or disubstituted by alkyl (1–4 C),
- $R_2$ and $R_3$ independently of one another are hydrogen or alkyl (1–4 C) and
- $R_4$ is hydrogen, hydroxy, alkyl (1–4 C), alkoxy (1–4 C) or halogen with an atomic number of 9 to 35, in free base or acid addition salt form, hereinafter referred to as new compounds.

Insofar as above-defined alkyl or alkoxy groups are present in the new compounds, these preferably have one or two carbon atoms and especially signify methyl or methoxy.

The imidazolylmethyl radical is preferably in position 2 of the pyridine.

$R_1$ is preferably methyl. $R_2$ and $R_3$ are preferably each hydrogen. $R_4$ is preferably hydrogen. The compound of Example 1 is preferred.

In a particular group of new compounds, $R_1$ is alkyl (1–4 C), $R_2$ and $R_3$ independently of one another are hydrogen or alkyl (1–4 C) and $R_4$ is hydrogen, alkyl (1–4 C) or halogen with an atomic number of 9 to 35.

In accordance with the invention, the new compounds are obtained by reacting a compound of formula II,

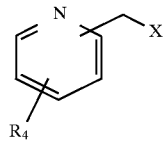

wherein $R_4$ is defined as above, and X is halogen, with a compound of formula III,

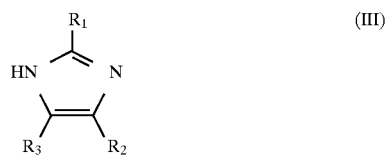

wherein $R_1$, $R_2$ and $R_3$ are defined as above,
and recovering the resulting compound of formula I in free base form or in acid addition salt form.

The reaction of a compound of formula II with a compound of formula III may take place in known manner, in a solvent which is inert under the reaction conditions, e.g. in dimethylformamide or a lower alcohol. In formula II, X is preferably chlorine.

Working up of the reaction mixtures obtained and purification of the compounds of formula I thus produced may take place in accordance with known methods.

The compounds of formula I may be present in free base form or in the form of their acid addition salts. Acid addition salts may be produced from the free bases in known manner, and vice versa.

The starting compounds of formula II and III are known or may be produced in accordance with known processes, resp. analogously to known processes.

The compounds of formula I and their physiologically acceptable salts, hereinafter referred to as compounds according to the invention, exhibit interesting pharmacological activities and may therefore be used as pharmaceuticals.

The compounds according to the invention have anti-depressant activity as evidenced by tests on the sleep/wake cycle in mammals, e.g. in the sleep/wake cycle of the long-term implanted rat [for the method, see J. -M. Vigouret et al., J. Pharmacol 10, 503 (1978)]. In this test the compounds according to the invention when administered at 1 to 100 mg/kg p.o. effect an increase in vigilance by prolonging the wake phases. Furthermore in the same test when administered at 1 to 100 mg/kg p.o. the compounds according to the invention reduce the REM sleep phases.

The test is based on the well-recognized finding that total sleep deprivation (which corresponds to prolongation of the wake phases) or selective REM sleep deprivation has an antidepressant effect (see for example W. B. Mendelson et al., Human Sleep and its Disorders, Plenum Press, New York and London, p. 173) and that various antidepressants suppress REM sleep in normal and depressed patients (same article, p. 178).

In this test the minimal effective dose of the compound of Example 1 is 3 mg/kg p.o.

Moreover, after administration of 1 to 100 mg/kg p.o. to rats with bilateral lesions of the Locus coeruleus (LC) and the Nucleus basalis Meynert (NBM), the compounds according to the invention improve significantly the cognitive performance as measured by the ability to avoid an electric shock in the shuttle box.

The method is similar to that described by V. Haroutunian et al. in Brain Research 507 (1990) 261–266. Male OFA rats (300 g) are anesthetized with pentobarbital and positioned in a stereotaxic apparatus with the upper incisor bar set 5 mm (LC) or 3.3 mm (NBM) below the interaural line. The lesions are carried out with a radio frequency lesion generator at 60° C. during 10 seconds. 5 weeks after lesioning, behavioral testing is performed, using the active avoidance test in the shuttle box as described by A. R. Dravid, A. -L. Jaton and E. B. Van Deusen in Experimental Brain Research, Suppl. 13, p. 249 (1986).

The double lesions test provides concomitant lesions of the cholinergic and noradrenergic systems and is based on literature indicating that deterioration of both systems in the brain contributes to the cognitive and memory deficits associated with senile dementia and Alzheimer's disease [see for example Decker M. W. and Gallagher M. in Brain Research, 417 (1987) 59–69 or the above-mentioned article of Haroutunian et al.].

The minimal effective dose of the compound of Example 1 in this double lesions test is 1 mg/kg p.o. At 10 mg/kg, the compound reestablishes the total number of right avoidance responses as obtained with the controls (sham operated rats).

The compounds according to the invention are therefore useful for the treatment of senile dementia, Alzheimer's disease and further degenerative diseases characterized by cholinergic and noradrenergic lesions such as Buntington's chorea, Morbus Parkinson, Steel-Richardson syndrome, tardive dyskinesias, hyperkinesia, acute confusion disorders, Down's syndrome, myasthenia gravis and Friedrich's ataxia, and furthermore as antidepressants.

The preferred indications are senile dementia, Alzheimer's disease and depression. The preferred compound is the compound of Example 1.

For these indications, the appropriate dosage will, of course, vary depending upon, for example, the compound employed, the host, the mode of administration and the nature and severity of the condition being treated. However, in general, satisfactory results in animals are indicated to be obtained at daily dosages from about 0.5 to about 50 mg/kg animal body weight. In larger mammals, for example humans, an indicated daily dosage is in the range from about 1 mg to about 100 mg of a compound according to the invention, conveniently administered, for example, in divided doses up to four times a day.

For the compound of Example 1, an indicated daily dosage for the above-mentioned preferred indications is from about 5 mg to about 30 mg.

The compounds according to the invention may be administered by any conventional route, in particular enterally, preferably orally, for example in the form of tablets or capsules, or parenterally, for example in the form of injectable solutions or suspensions.

For the antidepressant use the compound of Example 1 may be administered to larger mammals, for example humans, by similar modes of administration at similar dosages as conventionally employed with imipramine.

The present invention also provides pharmaceutical compositions comprising a compound according to the invention in association with at least one pharmaceutical carrier or diluent. Such compositions may be manufactured in conventional manner. Unit dosage forms contain, for example, from about 0.25 mg to about 50 mg of a compound according to this invention.

The present invention furthermore provides a method of treating senile dementia, Alzheimer's disease and further degenerative diseases such as Huntington's chorea, Morbus Parkinson, Steel-Richardson syndrome, tardive dyskinesias, hyperkinesia, acute confusion disorders, Down's syndrome, myasthenia gravis and Friedrich's ataxia, and of treating depression, in a subject in need of such treatment, which comprises administering a therapeutically effective amount of a compound according to the invention.

The following examples illustrate the invention. The temperatures are given in degrees Celsius and are uncorrected.

EXAMPLE 1

[2-(2-methylimidazol-1-yl)methyl]pyridine 9.7 g (75 mM) of 2-(chloromethyl)pyridine and 42 g (512 mM) of 2-methyl-imidazole are suspended in 40 ml dimethylformamide, then stirred for 3 hours at 105°. The dimethylformamide is distilled off and the crystalline residue is diluted with ethyl acetate and a little hexane. Following filtration, the mother solution is concentrated by evaporation and the dimethylformamide distilled off, and then shaken out several times between water and methylene chloride. 10.3 g of the oily title compound are obtained.

9.3 g of the obtained base in ethanol are mixed with 12.7 g of fumaric acid. The resulting bis(base)-tris(hydrogen fumarate)crystallizes from ethanol/ethyl acetate and is recrystallized once from ethanol/ethyl acetate. It is uniform upon thin-layer chromatography and melts at 109°–110°. The fumarate is obtained analogously and melts at 120°–121°.

The following [2-(imidazol-1-yl)methyl]pyridines are produced anagously to example 1:

| Example | $R_1$ | $R_2$ | $R_3$ | $R_4$ | M.p. |
|---|---|---|---|---|---|
| 2 | $CH_3$ | H | H | 6-$CH_3$ | 129–130° * |
| 3 | $CH_3$ | $CH_3$ | H | H | 250–253° (decomp.) ** |
| 4 | $CH_3$ | H | $CH_3$ | H | 213–220° (decomp.) ** |

\* fumarate
\*\* dihydrochloride as well as the following [4-(imidazol-1-yl)methyl]pyridine:

| Example | $R_1$ | $R_2$ | $R_3$ | $R_4$ | M.p. |
|---|---|---|---|---|---|
| 5 | $CH_3$ | H | H | H | 155–156° * |

\* fumarate

What we claim is:

1. A method of treating senile dementia of the Alzheimer's type comprising administering to a subject in need of such treatment a therapeutically effective amount of a compound having the formula

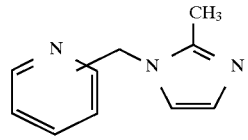

in free base or physiologically acceptable acid addition salt form.

2. A method according to claim 1 wherein the compound administered is in free base, hydrogen fumarate or fumarate salt form.

3. A method according to claim 1 wherein the compound administered is [2-(2-methylimidazol-1-yl-)methyl]pyridine, in free base or physiologically acceptable acid addition salt form.

4. A method according to claim 3 wherein the compound is administered in free base, hydrogen fumarate or fumarate salt form.

5. A method according to claim 4 wherein the compound administered is [2-(2-methylimidazol-1-yl)methyl]pyridine fumarate.

* * * * *